(12) United States Patent
James

(10) Patent No.: US 12,064,423 B2
(45) Date of Patent: Aug. 20, 2024

(54) MEDICINE COMBINATIONS AND TREATMENT OF RESTLESS LEG SYNDROME

(71) Applicant: MindLab LLC, New York, NY (US)

(72) Inventor: Lawrence R. James, New York, NY (US)

(73) Assignee: MindLab LLC, New York, NY (US)

( * ) Notice: Subject to any disclaimer, the term of this patent is extended or adjusted under 35 U.S.C. 154(b) by 1 day.

(21) Appl. No.: 17/304,414

(22) Filed: Jun. 21, 2021

(65) Prior Publication Data
US 2022/0211677 A1 Jul. 7, 2022

Related U.S. Application Data

(63) Continuation of application No. 16/332,866, filed as application No. PCT/US2017/051257 on Sep. 13, 2017, now abandoned.

(60) Provisional application No. 62/393,734, filed on Sep. 13, 2016.

(51) Int. Cl.
*A61K 31/439* (2006.01)
*A61K 31/4709* (2006.01)
*A61P 25/00* (2006.01)

(52) U.S. Cl.
CPC ........ *A61K 31/439* (2013.01); *A61K 31/4709* (2013.01); *A61P 25/00* (2018.01); *A61K 2300/00* (2013.01)

(58) Field of Classification Search
CPC .............. A61K 2300/00; A61K 31/138; A61K 31/439; A61K 31/4709; A61K 31/485; A61K 31/49; A61K 45/06; A61P 25/00; A61P 25/14; A61P 25/20
See application file for complete search history.

(56) References Cited

U.S. PATENT DOCUMENTS

| | | | |
|---|---|---|---|
| 5,698,155 A | 12/1997 | Grosswald et al. | |
| 6,136,839 A | 10/2000 | Isakson et al. | |
| 6,207,674 B1 | 3/2001 | Smith | |
| RE38,115 E | 5/2003 | Smith et al. | |
| 8,231,901 B2 | 7/2012 | Breder et al. | |
| 2007/0196481 A1 | 8/2007 | Amidon et al. | |
| 2009/0111846 A1 | 4/2009 | Berg | |
| 2010/0196269 A1 | 8/2010 | Dolle et al. | |
| 2010/0249045 A1 | 9/2010 | Babul | |
| 2012/0165363 A1 | 6/2012 | Yakatan et al. | |
| 2012/0172388 A1 | 7/2012 | Smith | |
| 2012/0231092 A1 | 9/2012 | Oronsky et al. | |
| 2014/0256763 A1 | 9/2014 | James et al. | |
| 2016/0030417 A1 | 2/2016 | James et al. | |

FOREIGN PATENT DOCUMENTS

| | | | |
|---|---|---|---|
| EP | 1535615 A1 | 6/2005 | |
| JP | 2004-043479 A | 2/2004 | |
| JP | 2005/306882 A | 11/2005 | |
| JP | 2012/116858 A | 6/2012 | |
| JP | 2012/131815 A | 7/2012 | |
| WO | 9848821 A2 | 11/1998 | |
| WO | WO 2001/013903 | * | 3/2001 |
| WO | 2004006930 A1 | 1/2004 | |

OTHER PUBLICATIONS

Morphine Dosages Retrieved from: Drugs.com [Retrieved on: Aug. 19, 2015] [May 2, 2010] <U rl:https ://web. archive.org/web/20 1 005021 61 713/http:/ /www.drugs.com/dosage/morph in e. html>.
Leavitt. Opioid ANtagonist in Pain Management. PPM Apr. 1, 2009, pp. 1-6.
Bell Combine and conquer: advantages and disadvantages of fixed-dose combination therapy( Diabetes, Obesity and Metabolism (2013), vol. 15, pp. 291-300; Published Online Oct. 2012) .
Samer et al., "The effects of CYP2D6 and CYP3A activities on the pharmacokinetics of immediate release oxycodone," British Journal of Pharmacology (201 0) 160:907-918.
Samer et al., "Genetic polymorphisms and drug interactions modulating CYP2D6 and CYP3A activities have a major effect on oxycodone analgesic efficacy and safety," British Journal of Pharmacology (201 0) 160:919-930.
Office Communication in U.S. Appl. No. 14/201,129 mailed Sep. 10, 2015.
Office Communication in U.S. Appl. No. 14/201,129, mailed Jun. 22, 2016.
Akerele et al., "Dextromethorphan and Quinidine Combination for Heroin Detoxification" Am J. Addict (2008), vol. 17, pp. 176-180.
Galer, "MorphiDex ® (morphine sulfate/dextromethorphan hydrobromide combination) in the treatment of chronic pain: Three multicenter, randomized, double-blind, controlled clinical trials fail to demonstrate enhanced opioid analgesia or reduction in tolerance" Pain 115 (2005) pp. 284-295.
Mercadante et al., Analgesic effect of intravenous ketamine in cancer patients on morphine therapy, Journal of Pain of Symptom Management 2000 20(4):246-252.
Weinbroum et al., Dextromethorphan for the reduction of immediate and late postoperative pain and morphine consumption in orthopedic oncology patients, Cancer 2002 95(5):1164-1170.
European Search Report dated Nov. 11, 2016 in EP Application No. 14760959.8.
Final Office Action in U.S. Appl. No. 14/772,128 mailed Nov. 15, 2017.
PubChem CID 5462351 [online] Retrieved on Nov. 6, 2017 Retrieved from internet url:https://pubchem.ncbi.nlm.nih.gov/compound/ Dextromethorphan_hydrobromide_monohydrate, (2016).

(Continued)

*Primary Examiner* — Kevin E Weddington
(74) *Attorney, Agent, or Firm* — Goodwin Procter LLP

(57) ABSTRACT

Embodiments disclosed herein describe, amongst other things, dosage forms, compounds, compositions, pharmaceutical compositions that can be used in the treatment of, for example, restless leg syndrome.

5 Claims, No Drawings

(56) References Cited

OTHER PUBLICATIONS

Notice of Allowance in U.S. Appl. No. 14/201,129 mailed Nov. 14, 2019.
Non-Final Office Actioon in U.S. Appl. No. 14/201,129, mailed Jul. 5, 2019.
Final Office Action in U.S. Appl. No. 16/676,770 mailed Jan. 25, 2022.
Kapur, et al., "Oral Ketamine: A Promising Treatment for Restless Legs Syndrome," Anesthesia and Analgesia, 2002, 94(6): pp. 1558-1559.
Bayard et als., "Bupropion and Restless Legs Syndrome: A Randomized Controlled Trial," Journal of The American Board of Family Medicine, , Jul.-Aug. 2011, vol. 24, No. 4, pp. 422-428.
Walters, et als., "Successful Treatmen of the Idiopathic Restless Legs Syndrome in a Randomized Double-Blind Trial of Oxycodone Versus Placebo," Sleep, vol. 16, No. 4, 1993, pp. 327-332.
Trenkwalder, et als., "Prolonged Release Oxycodone-Naloxone for Treatment of Severe Restless LEgs Syndrome after Failure of Previous Treatment: a Double-Blind, Randomised, Placebo-Controlled Trial with an Open-Label Extension," The Lancet Neurology, 12(12), Dec. 2013, pp. 1141-1140.

\* cited by examiner

MEDICINE COMBINATIONS AND TREATMENT OF RESTLESS LEG SYNDROME

CROSS-REFERENCE TO RELATED APPLICATIONS

The present application is a continuation of U.S. patent application Ser. No. 16/332,866, filed Mar. 13, 2019, now abandoned, which is a U.S. 371 national phase application of International Application No. PCT/US2017/051257, filed Sep. 13, 2017, which claims priority to U.S. Provisional Application No. 62/393,734, filed Sep. 13, 2016, the contents of each of which are hereby incorporated by reference in their entirety.

FIELD

Embodiments described herein relate to compositions and pharmaceutical compositions that can be used, for example, to treat or prevent restless leg syndrome.

BACKGROUND

Compounds that act in the brain require high levels in order to work efficiently due to many factors. This issue has been difficult to overcome for many medications because as levels are increased side effects also increase, some of which are severe and prevent the compound from being used effectively in a general population. Accordingly, there is a need to for products that can be used to treat various conditions with fewer side effects and/or better efficacy. The embodiments described herein provide for such compositions and methods with significant and unexpected advantages over previous compositions.

SUMMARY

In some embodiments, pharmaceutical compositions are provided. In some embodiments, the pharmaceutical composition comprises a NMDA antagonist, a CYP2D6 inhibitor; and an opioid agonist. In some embodiments, the opioid agonist is selected from the group consisting of tramadol, morphine, oxycodone, oxymorphone, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, myrophine, nalbuphine, narceine, nicomorphine, norlevorphanol, normethadone, nalorphine, normorphine, norpipanone, opium, papaveretum, pentazocine, phenadoxone, phenomorphan, phenazocine, phenoperidine, piminodine, piritramide, proheptazine, promedol, properidine, propiram, propoxyphene, sufentanil, tilidine, or a pharmaceutically acceptable salt thereof or a pharmaceutically acceptable salt thereof.

In some embodiments, pharmaceutical dosage forms are provided. In some embodiments, the dosage form comprises a NMDA antagonist, a CYP2D6 inhibitor, and an opioid agonist.

In some embodiments, methods of method of treating or preventing restless leg syndrome or symptoms thereof in a subject are provided. In some embodiments, the methods comprise administering to the subject a pharmaceutical composition or dosage form described herein.

DETAILED DESCRIPTION

Unless otherwise defined, all technical and scientific terms used herein have the same meaning as commonly understood by one of ordinary skill in the art. Although methods and materials similar or equivalent to those described herein can be used in the practice or testing of the compositions and compounds described herein, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the compositions and compounds described herein will be apparent from the following detailed description and claims.

Various compositions are described herein. Each of the compositions described herein can also be pharmaceutical compositions.

The present embodiments described herein provide compositions that unexpectedly and surprisingly treat or prevent restless leg syndrome or symptoms thereof. These symptoms include, but are not limited to, uncomfortable sensations in the legs and/or an irresistible urge to move their legs to relieve the sensations. Other symptoms include, but are not limited to, itchiness, a pins and needles feeling or a "creepy crawly" feeling in the legs. In some embodiments, a method of reducing the symptoms described herein are provided by administering the compositions and forms described herein. In some embodiments, the symptoms are completely reduced. In some embodiments, the symptoms are lessened but not completely eliminated. Thus, the methods and compositions described herein can used to treat the symptoms of restless leg syndrome by administering the compositions and forms described herein. In some embodiments, the compositions and forms described herein can be used to treat sleeplessness associated with restless leg syndrome. Thus, in some embodiments, methods of improving sleep or inducing sleep in a subject with restless leg syndrome are provided by administering the compositions and forms described herein. The surprising results are from the combination of three compounds, an opioid agonist, such as an opioid agonist, a CYP2D6 inhibitor, and a NMDA antagonist. Without being bound to any particular theory, the combination of the three types of compounds allow the combination of compounds to be effective at levels to treat or prevent restless leg syndrome and its symptoms as compared to just one or two of the compounds. Therefore, a smaller amount of the opioid agonist should be able to be used, leading to fewer side effects or a similar amount of the opioid agonist as was used prior to the present application with better results. In some embodiments, the compositions have an effect that is longer in duration than the opioid agonist alone. In some embodiments, the compositions also have a lower incidence of tolerance. For example, in regards to the compositions described herein, the compositions can have a lower incidence of tolerance, thereby keeping the amount of the opioid agonist to a minimum, which can reduce one or more of the adverse side effects that are common to the usage of opioid agonists. The advantages described herein can also apply to having all three components (e.g. opioid agonist, NMDA antagonists, and CYP2D6 inhibitor) administered or present in a composition as opposed to just two of an opioid agonist, dextromethorphan or CYP2D6 inhibitor. In some embodiments, the combination of an opioid agonist, NMDA antagonist, and CYP2D6 inhibitor has other reduced side effects compared to any of the components alone or in a combination of just two of them. Examples of side effects that are reduced or ameliorated include, but are not limited to, increase in blood sugar, tremors, anxiety, increase in cholesterol, unusual/uncontrolled movements, increase in prolactin, fainting, seizures, muscle spasms, fatigue, weight gain, weight loss, constipation, diarrhea, nausea, vomiting, stomach pain, loss of appetite, flushing (e.g. warmth, redness, or tingly feeling), headache, dizziness, spinning sensation, memory problems, sleep problems (insomnia), strange dreams, drowsiness, lightheadedness, drooling, hallucination, nightmares, itchiness, hives, delusional perception, malaise, dry mouth, and the like. Therefore, the compositions described herein can reduce or lessen one or more of these side effects. In some embodiments, the one or more side effects that are reduced are associated with the opioid agonist (e.g. oxycodone or oxymorphone).

Accordingly, in some embodiments, compositions are provided that comprise an an opioid agonist, a NMDA antagonists, and a CYP2D6 inhibitor. In some embodiments, the composition comprises an opioid agonist, dextromethorphan, quinidine, pharmaceutically acceptable salt of each or any of the foregoing, or any combination thereof is provided. In some embodiments, the opioid agonist is oxycodone. In some embodiments, the opioid agonist is an opioid agonist. Examples of opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts of each or any of the foregoing, and any mixtures thereof. In some embodiments, the opioid agonist is morphine, oxycodone, and hydromorphone, or a pharmaceutically acceptable salt thereof, or any combination thereof. In some embodiments, the morphine is morphine sulfate.

In some embodiments, the NMDA antagonist is chosen from one or more of dextromethorphan, a glycine antagonist, ifenprodil or ifenprodil like compounds, amantadine, MK-801 (dizocilpine; [5R,10S]-[+]-5-methyl-10,11-dihydro-5H-dibenzo[a,d]cyclohepten-5,10-imine), ketamine, memantine, D-AP5 (D(−)-2-Amino-5-phosphonovaleric acid), CPP (3-(2-Carboxypiperazin-4-yl)propyl-1-phosphonic acid), or a pharmaceutically acceptable salt thereof, or any combination thereof. In some embodiments, the NMDA antagonist is dextromethorphan. Examples of glycine antagonist include, but are not limited to, GLYX-13, TK-40, 1-Aminocyclopropanecarboxylic acid (ACPC), 7-Chlorokynurenic acid, DCKA (5,7-dichlorokynurenic acid), kynurenic acid, lacosamide, L-phenylalanine, and the like. The compositions and dosage forms described herein can have one or more of the glycine antagonists. In some embodiments, the dextromethorphan is a hydrate, such as but not limited to, dextromethorphan hydrobromide monohydrate.

In some embodiments, the CYP2D6 inhibitor chosen from one or more of: quinidine, methadone, bupropion, cinacalcet, fluoxetine, paroxetine, duloxetine, sertraline, terbinafine, amiodarone, cimetidine, or a pharmaceutically acceptable salt thereof, or any combination thereof. In some embodiments, the CYP2D6 inhibitor is quinidine or a pharmaceutically acceptable salt thereof.

In some embodiments, the composition is formulated for simultaneous administration. As used herein "simultaneous administration," as it refers to a composition comprising more than one active ingredient or therapeutic agent, means that each of the active ingredients or therapeutic agents are administered substantially or exactly at the same time. The agents may be absorbed or become bioavailable at different rates or times, but the administration of the components, ingredients, or agents, is simultaneous. In some embodiments, the administration is not simultaneous. Simultaneous administration can be achieved by having each of the components (e.g., opioid agonist, NDMA antagonist, and CYP2D6 inhibitor) in the same dosage form. Simultaneous administration can also be achieved where each of the components are not in the same dosage form, but are administered substantially or exactly at the same time.

The ratio of the different components present in the composition can also be altered. In some embodiments, the ratio of the opioid agonist to NMDA antagonist is about 1:1 (wt:wt). In some embodiments, the ratio of the opioid agonist to NMDA antagonist is about 0.1 to 1:1 (wt:wt). In some embodiments, the ratio of the opioid agonist to NMDA antagonist is about 0.5 to 1:1 (wt:wt). In some embodiments, the ratio of the opioid agonist to NMDA antagonist is about 0.7 to 1:1 (wt:wt). In some embodiments, the ratio of the opioid agonist to NMDA antagonist is about 0.8 to 1:1 (wt:wt). In some embodiments, the ratio of the opioid agonist to NMDA antagonist is about 0.9 to 1:1 (wt:wt). In some embodiments, the ratio of the opioid agonist to CYP2D6 inhibitor is about 1:0.1 to 1:1 (wt:wt). In some embodiments, the ratio of the opioid agonist to CYP2D6 inhibitor is about 1:0.2 to 1:1 (wt:wt). In some embodiments, the ratio of the opioid agonist to CYP2D6 inhibitor is about 1:0.3 to 1:1 (wt:wt). In some embodiments, the ratio of the opioid agonist to CYP2D6 inhibitor is about 1:0.4 to 1:1 (wt:wt). In some embodiments, the ratio of the opioid agonist to CYP2D6 inhibitor is about 1:0.4 to 1:1 (wt:wt). In some embodiments, the ratio of the opioid agonist to CYP2D6 inhibitor is about 1:0.5 to 1:1 (wt:wt). In some embodiments, the ratio of the opioid agonist to CYP2D6 inhibitor is about 1:0.6 to 1:1 (wt:wt). In some embodiments, the ratio of the opioid agonist to CYP2D6 inhibitor is about 1:0.7 to 1:1 (wt:wt). In some embodiments, the ratio of the opioid agonist to CYP2D6 inhibitor is about 1:0.8 to 1:1 (wt:wt). In some embodiments, the ratio of the opioid agonist to CYP2D6 inhibitor is about 1:0.9 to 1:1 (wt:wt). In some embodiments, the ratio of the opioid agonist to NMDA antagonist to CYP2D6 inhibitor is 1:1:0.1-1 (wt:wt:wt). In some embodiments, the ratio of the opioid agonist to NMDA antagonist to CYP2D6 inhibitor is about 1:1:0.9-1.5 (wt:wt:wt). In some embodiments, the ratio of the opioid agonist to NMDA antagonist to CYP2D6 inhibitor is about 0.9-1.1:

0.9-1.1:0.9-1.5 (wt:wt:wt). In some embodiments, the amount of CYP2D6 inhibitor is in an effective amount to enhance the therapeutic effect of the opioid agonist alone or in combination with the NMDA antagonist. In some embodiments, the effective amount of the CYP2D6 inhibitor enhances the therapeutic effect of the opioid agonist alone or in combination with the NMDA antagonist at least 1.5, 2, 2.5, 3, 4, or 5 times. The enhancement can be compared in a non-human animal model or in a human study. In some embodiments the ratio of the opioid agonist to CYP2D6 inhibitor is about, or at least, 0.1:1, about, or at least, 0.2:1, about, or at least, 0.3:1, about, or at least, 0.4:1, about, or at least, 0.5:1, about, or at least, 0.6:1, about, or at least, 0.7:1, about, or at least, 0.8:1, about, or at least, 0.9:1, about, or at least, 1:1, about, or at least, 2:1, about, or at least, 3:1 and the like. In some embodiments, the ratio of the opioid agonist to CYP2D6 inhibitor is about 0.1-1:1, about 0.2-1:1, about 0.3-1:1, about 0.4-1:1, about 0.5-1:1, about 0.6-1:1, about 0.7-1:1, about 0.8-1:1, about 0.9-1:1, or about 1-2:1, or about 1-3:1, or about 1-4:1, or about 1-5:1.

In some embodiments, the ratio of the opioid agonist to dextromethorphan is about 1:1 (wt:wt). In some embodiments, the ratio of the opioid agonist to dextromethorphan is about 0.1 to 1:1 (wt:wt). In some embodiments, the ratio of the opioid agonist to dextromethorphan is about 0.5 to 1:1 (wt:wt). In some embodiments, the ratio of the opioid agonist to dextromethorphan is about 0.7 to 1:1 (wt:wt). In some embodiments, the ratio of the opioid agonist to dextromethorphan is about 0.8 to 1:1 (wt:wt). In some embodiments, the ratio of the opioid agonist to dextromethorphan is about 0.9 to 1:1 (wt:wt). In some embodiments, the ratio of the opioid agonist to quinidine is about 1:0.1 to 1:1 (wt:wt). In some embodiments, the ratio of the opioid agonist to quinidine is about 1:0.2 to 1:1 (wt:wt). In some embodiments, the ratio of the opioid agonist to quinidine is about 1:0.3 to 1:1 (wt:wt). In some embodiments, the ratio of the opioid agonist to quinidine is about 1:0.4 to 1:1 (wt:wt). In some embodiments, the ratio of the opioid agonist to quinidine is about 1:0.4 to 1:1 (wt:wt). In some embodiments, the ratio of the opioid agonist to quinidine is about 1:0.5 to 1:1 (wt:wt). In some embodiments, the ratio of the opioid agonist to quinidine is about 1:0.6 to 1:1 (wt:wt). In some embodiments, the ratio of the opioid agonist to quinidine is about 1:0.7 to 1:1 (wt:wt). In some embodiments, the ratio of the opioid agonist to quinidine is about 1:0.8 to 1:1 (wt:wt). In some embodiments, the ratio of the opioid agonist to quinidine is about 1:0.9 to 1:1 (wt:wt). In some embodiments, the ratio of the opioid agonist to dextromethorphan to quinidine is 1:1:0.1-1 (wt:wt:wt). In some embodiments, the ratio of the opioid agonist to dextromethorphan to quinidine is about 1:1:0.9-1.5 (wt:wt:wt). In some embodiments, the ratio of the opioid agonist to dextromethorphan to quinidine is about 0.9-1.1:0.9-1.1:0.9-1.5 (wt:wt:wt). In some embodiments, the amount of quinidine is in an effective amount to enhance the therapeutic effect of the opioid agonist and dextromethorphan without the quinidine. In some embodiments, the effective amount of quinidine enhances the therapeutic effect of opioid agonist and dextromethorphan at least 1.5, 2, 2.5, 3, 4, or 5 times. The enhances can be compared in a non-human animal model, such as the tail flick model, or in a human study where subjects are asked to quantify the pain relief. In some embodiments the ratio of the opioid agonist to quinidine is about, or at least, 0.1:1, about, or at least, 0.2:1, about, or at least, 0.3:1, about, or at least, 0.4:1, about, or at least, 0.5:1, about, or at least, 0.6:1, about, or at least, 0.7:1, about, or at least, 0.8:1, about, or at least, 0.9:1, about, or at least, 1:1, about, or at least, 2:1, about, or at least, 3:1 and the like. In some embodiments, the ratio of the opioid agonist to quinidine is about 0.1-1:1, about 0.2-1:1, about 0.3-1:1, about 0.4-1:1, about 0.5-1:1, about 0.6-1:1, about 0.7-1:1, about 0.8-1:1, about 0.9-1:1, or about 1-2:1, or about 1-3:1, or about 1-4:1, or about 1-5:1.

In some embodiments, the ratio of the NMDA antagonist to the CYP2D6 inhibitor is about 1:1, about 2:1, about 1:2 or any ratio between. The ratio of the opioid agonist can also be as provided herein while keeping the ratio of the NMDA antagonist to the CYP2D6 constant as described in this section. In some embodiments, the ratio of the opioid agonist is about 2-10, about 2-8, about 2-6, about 2-5, about 2-4, or about 2-3 times as much as the NMDA antagonist.

In some embodiments, the composition comprises about 10 mg, about 20 mg, about 30 mg, about 40 mg, about 50 mg, about 60 mg of the opioid agonist. In some embodiments, the composition comprises from about 10 to about 100 mg, from about 10 to about 90 mg, from about 10 to about 80 mg, from about 10 to about 70 mg, from about 10 to about 60 mg, from about 10 to about 50 mg, from about 10 to about 40 mg, from about 10 to about 30 mg, from about 10 to about 20 mg, from about 20 to about 100 mg, from about 20 to about 90 mg, from about 20 to about 80 mg, from about 20 to about 70 mg, from about 20 to about 60 mg, from about 20 to about 50 mg, from about 20 to about 40 mg, from about 20 to about 30 mg, from about 30 to about 100 mg, from about 30 to about 90 mg, from about 30 to about 80 mg, from about 30 to about 70 mg, from about 30 to about 60 mg, from about 30 to about 50 mg, from about 30 to about 40 mg, from about 40 to about 100 mg, from about 40 to about 90 mg, from about 40 to about 80 mg, from about 40 to about 70 mg, from about 40 to about 60 mg, from about 40 to about 50 mg, from about 50 to about 100 mg, from about 50 to about 90 mg, from about 50 to about 80 mg, from about 50 to about 70 mg, from about 50 to about 60 mg, from about 60 to about 100 mg, from about 60 to about 90 mg, from about 60 to about 80 mg, from about 60 to about 70 mg, from about 70 to about 100 mg, from about 70 to about 90 mg, from about 70 to about 80 mg, from about 80 to about 100 mg, from about 80 to about 90 mg, or from about 90 to about 100 mg.

In some embodiments, the composition comprises an opioid agonist selected from the group consisting of oxycodone and an opioid agonist.

As discussed herein, in some embodiments, the oral dosage form can comprise an active ingredient antagonist. In some embodiments, the oral dosage form comprises a sequestered active ingredient antagonist. A sequestered active ingredient antagonist is one that is not bioavailable unless the oral dosage form is tampered with or adulterated. Active agents can be abused for their euphoric effect and if the dosage form is a controlled release or sustained release dosage form, crushing the dosage form can increase the bioavailability of the opioid agonist. Therefore, to prevent abuse, the dosage form can be made with an active ingredient antagonist such that the activity of opioid agonist is inhibited if the dosage form is altered, adulterated or tampered with by the subject using the dosage form. Therefore, in some embodiments, the oral dosage form further comprises a sequestered active agent antagonist which is not released when the dosage form is administered intact. In some embodiments, the sequestered antagonist is in an amount which will negate the euphoric effect of the opioid agonist when the dosage form is tampered with and misused by a human. The form can be misused by administering the tampered dosage form orally, parenterally, intranasally or sublingually. In some embodiments, the sequestered antagonist is selected from the group consisting of naltrexone, naloxone, nalmefene, cyclazocine, levallorphan, pharmaceutically acceptable salts thereof and mixtures thereof. Other examples of sequestered antagonists and formulations thereof are described in U.S. Pat. No. 8,231,901, which is hereby incorporated by reference. In some embodiments, the antagonist is an opioid antagonist.

Also provided herein are methods of treating or preventing restless leg syndrome comprising administering to a subject a composition or pharmaceutical composition described herein. The compositions, dosage forms, and such described herein, can be used to ameliorate a symptom of restless leg syndrome.

In some embodiments, the restless leg syndrome symptoms are uncomfortable sensations in a person's leg, an irresistible urge to move their legs to relieve the sensations, itchiness in the leg, the sensation of pins and needles in the legs, throbbing, pain, tugging, gnawing, burning, and the like. In some embodiments, the compositions are used to prevent nighttime twitching of the legs. In some embodiments, the compositions are used to release the urge to move the legs to relieve the symptoms of restless leg syndrome. In some embodiments, the symptoms of restless leg syndrome are treated or prevented with a composition comprising an opioid agonist, a NMDA antagonist, and a CYP2D6 inhibitor. In some embodiments, the NMDA antagonist is dextromethorphan, or a pharmaceutically acceptable salt thereof. In some embodiments, the CYP2D6 inhibitor is quinidine. In some embodiments, the opioid agonist is oxycodone, oxymorphone, hydrocodone, tramadol, tilidine, dihydrocodeine, codeine, propoxyphene, or methadone.

In some embodiments, the composition or pharmaceutical composition or dosage form is administered every 2 hours, 4 hours, every 6 hours, every 8 hours, every 12 hours, or every 24 hours. In some embodiments, the composition or pharmaceutical composition or dosage form is administered 1, 2, 3, or 4 times a day.

In some embodiments, the subject (patient) has been previously treated for restless leg syndrome. In some embodiments, the subject is a subject in need thereof. In some embodiments, the method comprises treating restless leg syndrome patient that suffers from augmentation of restless leg syndrome. Augmentation can be referred to as the worsening of symptoms of restless leg syndrome due to ongoing treatment for restless leg syndrome. In some embodiments, the subject is treated with less opioid agonist as the subject was previously treated with for restless leg syndrome. In some embodiments, the subject is treated with a combination of NMDA antagonist; a CYP2D6 inhibitor; and an opioid agonist, wherein the opioid agonist is reduced about, or at least, 10%, 20%, 30%, 40%, 50%, 60%, 70%, 80%, or 90% as compared to when the opioid agonist is used with one or both of the NMDA antagonist and the CYP2D6 inhibitor. In some embodiments, the subject is treated with a combination of NMDA antagonist; a CYP2D6 inhibitor; and an opioid agonist, wherein the opioid agonist is reduced about 10% to about 90%, about 10% to about 80%, about 10% to about 70%, about 10% to about 80%, about 10% to about 70%, about 10% to about 60%, about 10% to about 50%, about 30 to about 60%, about 40% to about 60%, or about 50% to about 75% as compared to when the opioid agonist is used with one or both of the NMDA antagonist and the CYP2D6 inhibitor. In some embodiments, the amount of opioid agonist is less in a subject that suffers from augmentation of restless leg syndrome.

Due to the potential for abuse, many active ingredients are administered in conjunction with a risk evaluation mitigation strategy (REMS). A REMS can include a medication guide, patient package insert, a communication plan, elements to assure safe use, an implementation system, or any combination thereof. Because the compositions described herein may use less amounts of the opioid agonist, risk evaluation mitigation strategies may not need to be used. Therefore, in some embodiments, the method does not comprise the use of a risk evaluation mitigation strategy or any element of a REMS, some of which are described herein.

In some embodiments, in addition to the components described herein, the composition can comprise non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable agents that can be used include, but not limited to, the following chemical classes of analgesic, antipyretic, non-steroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, Analgesic Antipyretic and Antiinflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti Inflammatory Drugs in Remington: The Science and Practice of Pharmacy Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839. Cox II inhibitors include, but are not limited to, rofecoxib and celecoxib.

The compositions described herein can also comprise antimigraine agents, which include but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

Any pain treated, ameliorated, or prevented in accordance with the methods described herein can be acute pain or chronic pain, such as, but not limited to, nociceptive pain, neuropathic pain and psychogenic pain, and can be cancer related or not associated with cancer. Example of "nociceptive pain" include, but are not limited to, pain caused by injury to body tissues, including, without limitation, by a cut, bruise, bone fracture, crush injury, burn, surgery, and the like. In some embodiments, the pain is somatic pain. The term "somatic pain" is used to refer to pain arising from bone, joint, muscle, skin, or connective tissue. This type of pain is typically aching or throbbing in quality and is well localized. The term "neuropathic pain" is used herein to refer to pain originating from abnormal processing of sensory input by the peripheral or central nervous system. The pain can also be as a result of surgery, which can be referred to as post-surgical pain. Examples of surgery include, but are not limited to, dental or trauma, orthopedic surgery, and the like. The compositions described herein can be used, in some embodiments, to treat or prevent these types of pain as well as others.

The compositions described herein can also be administered in a therapeutically effective amount to treat, ameliorate, or prevent restless leg syndrome. In some embodiments, the compositions described herein are administered to produce enhanced therapeutic effects as compared to the opioid agonist given alone or in combination with NMDA antagonist, but without a CYP2D6 inhibitor. In some embodiments, the NMDA antagonist is one described herein, including, but not limited to dextromethorphan. In some embodiments, the CYP2D6 inhibitor is one described herein, including, but not limited to, quinidine. In some embodiments, the therapeutic effect is increased by at least 2-3 times when the opioid agonist is administered in combination with CYP2D6 inhibitor and NMDA antagonist as compared to just the opioid agonist alone or as compared to the opioid agonist in combination with NMDA antagonist. In some embodiments, none of the components (i.e. opioid agonist, NMDA antagonist, or CYP2D6 inhibitor) of a pharmaceutical composition are administered to the subject to avoid withdrawal symptoms. In some embodiments, for the compositions described herein, the different components are administered to treat, ameliorate, or prevent restless leg syndrome. That is, in some embodiments, the compositions, or dosage forms are administered with the intent treat or alleviate the symptoms of restless leg syndrome and not for the intent to avoid or treat withdrawal symptoms that can be associated with addiction.

As described herein, the pharmaceutical compositions can be administered in a dosage form. In some embodiments, the dosage form comprises an opioid agonist, a NMDA antagonist and a CYP2D6 inhibitor. In some embodiments, the dosage form comprises each of the components in the ratios described herein. In some embodiments, the dosage form is a pill, capsule, tablet, fast dissolving tablet (e.g. reditab and the like), liquid, film, fast dissolving film, which can also be referred to as oral wafers or oral films. Examples of these are described in Int J Pharm Investig. 2013 April-June; 3(2): 67-76, Curr Drug Deliv. 2013 December; 10(6):667-84, Curr Drug Deliv. 2013 February; 10(1):96-108, Curr Drug Deliv. 2011 July; 8(4):373-80, Curr Drug Deliv. 2009 October; 6(5):469-76, each of which is hereby incorporated by reference. In some embodiments, the compositions described herein are a dosage form. A dosage form is where each of the active ingredients or components are mixed together prior to administration. Examples of dosage forms are described herein and include, but are not limited to, pills, capsule, liquid, tablet, and the like. The dosage form can have the same components as discussed herein for the compositions. The ratios of the components can also be the same. In some embodiments, the dosage form is suitable for oral administration, topical administration, or parenteral administration. The compositions or dosage forms can also be administered sublingually, bucally, intranasal, and the like. The compositions described herein can be administered by any suitable method. In some embodiments, the composition is swallowed. In some embodiments, the composition is not swallowed. The composition may also be, for example, administered subcutaneously, intramuscularly, intravenously, transdermally or vaginally. In some embodiments, the combination of the opioid agonist, NMDA antagonist, and CYP2D6 inhibitor is administered simultaneously, separately, or a combination thereof. Therefore, in some embodiments, CYP2D6 inhibitor is administered before the opioid agonist or NMDA antagonist. In some embodiments, the CYP2D6 inhibitor is administered with the opioid agonist and then followed by the administration of NMDA antagonist. In some embodiments, CYP2D6 inhibitor is administered with NMDA antagonist and then followed by the administration of the opioid agonist. In some embodiments, each component is administered sequentially in any order. In some embodiments, they are administered concurrently in the same dosage form or in separate dosage forms.

In some embodiments, the compositions can be administered to a subject, animal, patient, or mammal in need thereof. As used herein, the phrase "in need thereof" means that the animal, subject, patient or mammal has been identified as having a need for the particular method, use, or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. As described herein, in some embodiments, the need, or intent, is to treat, ameliorate, or prevent restless leg syndrome.

As used herein, the term "mammal" means a rodent (i.e., a mouse, a rat, or a guinea pig), a monkey, a cat, a dog, a cow, a horse, a pig, or a human. In some embodiments, the mammal is a human. In some embodiments, the mammal is a non-human mammal.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

By "pharmaceutical formulation" or "pharmaceutical composition" it is further meant that the carrier, solvent, excipients and salt must be compatible with the active ingredient of the formulation (e.g. a compound described herein). It is understood by those of ordinary skill in this art that the terms "pharmaceutical formulation" and "pharmaceutical composition" are generally interchangeable, and they are so used for the purposes of this application. As discussed herein, the composition described herein can be a pharmaceutical composition. The composition can also have a pharmaceutically acceptable salt of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic. The present disclosure includes pharmaceutically acceptable salts of any compound(s) described herein.

Pharmaceutically acceptable salts can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile, and the like. Lists of suitable salts are found in Remington's Pharmaceutical Sciences, 18th ed., Mack Publishing Company, Easton, PA, USA, p. 1445 (1990).

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" includes any effect e.g., lessening, reducing, modulating, or eliminating, that results in the improvement of the condition, disease, disorder, etc. "Treating" or "treatment" of a disease state means the treatment of a disease-state in a mammal, such as in a human, and include: (a) inhibiting an existing disease-state, i.e., arresting its development or its clinical symptoms; and/or (c) relieving the disease-state, i.e., causing regression of the disease state. For example, with regards to symptoms described herein, the treatment of the symptoms would be the reduction of the symptom that one would have in the absence of the composition being administered. For example, in some embodiments, the terms "treatment of" and "treating" a symptoms include the lessening of the severity of or cessation of the symptoms. In some embodiments, it refers to decreasing the overall frequency of episodes of the symptom.

As used herein, "preventing" means causing the clinical symptoms of the disease state not to develop i.e., inhibiting the onset of disease, in a subject that may be exposed to or predisposed to the disease state, but does not yet experience or display symptoms of the disease state.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to the methods described herein. The compositions can also be administered in a therapeutically effective amount.

The present compositions, which includes dosage forms, can optionally comprise a suitable amount of a pharmaceutically acceptable excipient so as to provide the form for proper administration to the animal. Such pharmaceutical excipients can be, but not limited to, liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can, for example, take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in Remington's Pharmaceutical Sciences 1447-1676 (Alfonso R. Gennaro ed., 19th ed. 1995), incorporated herein by reference.

The compositions described herein can also be formulated to be a controlled- or sustained-release pharmaceutical compositions. Advantages of controlled- or sustained-release compositions include extended activity of the drug or combination of drugs, reduced dosage frequency, and increased patient compliance. In addition, controlled- or sustained-release compositions can favorably affect the time of onset of action or other characteristics, such as blood levels of the compounds, and can thus reduce the occurrence of adverse side effects.

For example, controlled- or sustained-release compositions can initially release an amount of the composition or component that promptly produces the desired therapeutic or prophylactic effect, and gradually and continually release other amounts of the composition or component to maintain this level of therapeutic or prophylactic effect over an extended period of time. To maintain a constant level of the composition or components, the composition or the individual components can be released from the dosage form at a rate that will replace the amount of composition or individual components being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

All percentages and ratios used herein, unless otherwise indicated, are by weight.

Throughout the description, where compositions are described as having, including, or comprising specific components, or where processes are described as having, including, or comprising specific process steps, it is contemplated that compositions described herein also consist essentially of, or consist of, the recited components, and that the processes described herein also consist essentially of, or consist of, the recited processing steps. Further, it should be understood that the order of steps or order for performing certain actions are immaterial so long as the process remains operable. Moreover, two or more steps or actions can be conducted simultaneously. Compositions can also refers to the dosage forms.

Embodiments provided herein also include, but are not limited to:

1. A method of treating or preventing restless leg syndrome or symptoms thereof in a subject comprising administering to the subject a pharmaceutical composition or a pharmaceutical dosage form comprising a NMDA antagonist; a CYP2D6 inhibitor; and an opioid agonist.
2. The method of embodiment 1, wherein the subject suffers from augmentation of restless leg syndrome.
3. The method of embodiments 1 or 2, wherein the opioid agonist is tramadol, morphine, oxycodone, oxymorphone, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, myrophine, nalbuphine, narceine, nicomorphine, norlevorphanol, normethadone, nalorphine, normorphine, norpipanone, opium, papaveretum, pentazocine, phenadoxone, phenomorphan, phenazocine, phenoperidine, piminodine, piritramide, proheptazine, promedol, properidine, propiram, propoxyphene, sufentanil, tilidine, or a pharmaceutically acceptable salt thereof.
4. The method of any one of embodiments 1-3, wherein the opioid agonist is tramadol, morphine, oxycodone, oxymorphone, or a pharmaceutically acceptable salt thereof.
5. The method of any one of embodiments 1-4, wherein the NMDA antagonist is chosen from one or more of dextromethorphan, a glycine antagonist, ifenprodil like compound, amantadine, MK-801 (dizocilpine; [5R,10S]-[+]-5-methyl-10,11-dihydro-5H-dibenzo[a,d]cyclohepten-5,10-imine), ketamine, memantine, D-AP5 (D(-)-2-Amino-5-phosphonovaleric acid) and, CPP (3-(2-Carboxypiperazin-4-yl)propyl-1-phosphonic acid), or a pharmaceutically acceptable salt thereof, or any combination thereof.
6. The method of any one of embodiments 1-5, wherein the NMDA antagonist is dextromethorphan, or a pharmaceutically acceptable salt thereof.
7. The method of any one of embodiments 1-6, wherein the NMDA antagonist is dextromethorphan hydrobromide monohydrate.
8. The method of any one of embodiments 1-7, wherein the CYP2D6 inhibitor is chosen from one or more of: quinidine, bupropion, cinacalcet, fluoxetine, paroxetine, duloxetine, sertraline, terbinafine, amiodarone, and cimetidine, or a pharmaceutically acceptable salt thereof, or any combination thereof.
9. The method of any one of embodiments 1-8, wherein the CYP2D6 inhibitor is quinidine, or a pharmaceutically acceptable salt thereof.
10. The method of any one of embodiments 1-6, wherein the CYP2D6 inhibitor is quinidine gluconate or quinidine sulfate.
11. The method of any one of embodiments 1-9, wherein the pharmaceutical composition is formulated for simultaneous administration.
12. The method of any one of embodiments 1-11, wherein the ratio of the opioid agonist to NMDA antagonist is about 1:1 (wt:wt).
13. The method of any one of embodiments 1-11, wherein the ratio of the opioid agonist to CYP2D6 inhibitor is about 1:0.1 to 1 (wt:wt).
14. The method of any one of embodiments 1-11, wherein the ratio of the opioid agonist to CYP2D6 inhibitor is about 0.1-1:1 (wt:wt).
15. The method of any one of embodiments 1-11, wherein the ratio of the opioid agonist to NMDA antagonist to CYP2D6 inhibitor is 1:1:0.1-1 (wt:wt:wt).
16. The method of any one of embodiments 1-15, wherein the ratio of the opioid agonist to NMDA antagonist to CYP2D6 inhibitor is about 1:1:1 (wt:wt:wt).
17. The method of any one of embodiments 1-16, wherein the pharmaceutical composition comprises about 10 mg, about 20 mg, about 30 mg, about 40 mg, about 50 mg, or about 60 mg of the opioid agonist.
18. The method of any one of embodiments 1-17, wherein the pharmaceutical composition further comprise an opioid antagonist.
19. The method of any one of embodiments 1-18, wherein the pharmaceutical composition is a dosage form.
20. The method of any one of embodiments 1-19, wherein said dosage form is an oral dosage form.
21. The method of any one of embodiments 1-19, wherein said dosage form is a fast-dissolving film.
22. The method of any one of embodiments 1-21, wherein the dosage form further comprises a sequestered opioid antagonist which is not released when the dosage form is administered intact.
23. The method of embodiment 22, said sequestered opioid antagonist is chosen from one or more of: naltrexone, naloxone, nalmefene, cyclazocine, and levallorphan, or a pharmaceutically acceptable salt thereof, or any combination thereof.
24. The method of any one of embodiments 1-23, wherein the pharmaceutical composition is administered every 4 hours, every 6 hours, every 8 hours, every 12 hours, or every 24 hours.

25. The method of any one of embodiments 1-24, wherein the amount of the opioid agonist is less than when the opioid agonist is administered without one or more of the NMDA antagonist and the CYP2D6 inhibitor.

26. A method of inducing or increasing sleep in a subject with restless leg syndrome, the method comprising administering to the subject a pharmaceutical composition or a pharmaceutical dosage form comprising a NMDA antagonist; a CYP2D6 inhibitor; and an opioid agonist.

27. The method of embodiment 26, wherein NMDA antagonist is chosen from one or more of dextromethorphan, a glycine antagonist, ifenprodil like compound, amantadine, MK-801 (dizocilpine; [5R,10S]-[+]-5-methyl-10,11-dihydro-5H-dibenzo[a,d]cyclohepten-5,10-imine), ketamine, memantine, D-AP5 (D(−)-2-Amino-5-phosphonovaleric acid) and, CPP (3-(2-Carboxypiperazin-4-yl)propyl-1-phosphonic acid), or a pharmaceutically acceptable salt thereof, or any combination thereof.

28. The method of embodiments 26 or 27, wherein the CYP2D6 inhibitor is chosen from one or more of: quinidine, bupropion, cinacalcet, fluoxetine, paroxetine, duloxetine, sertraline, terbinafine, amiodarone, and cimetidine, or a pharmaceutically acceptable salt thereof, or any combination thereof.

29. The method of any one of embodiments 25-27, wherein the opioid agonist is tramadol, morphine, oxycodone, oxymorphone, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, myrophine, nalbuphine, narceine, nicomorphine, norlevorphanol, normethadone, nalorphine, normorphine, norpipanone, opium, papavereturn, pentazocine, phenadoxone, phenomorphan, phenazocine, phenoperidine, piminodine, piritramide, proheptazine, promedol, properidine, propiram, propoxyphene, sufentanil, tilidine, or a pharmaceutically acceptable salt thereof.

30. The method of embodiment 26, wherein the NMDA antagonist is dextromethorphan, or a pharmaceutically acceptable salt thereof, the CYP2D6 inhibitor is quinidine, or a pharmaceutically acceptable salt thereof, and the opioid agonist is tramadol, morphine, oxycodone, oxymorphone, or a pharmaceutically acceptable salt thereof.

31. The method of embodiment 30, wherein the opioid agonist is tramadol or a pharmaceutically acceptable salt thereof.

32. The method of embodiment 30, the opioid agonist is morphine or a pharmaceutically acceptable salt thereof.

As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the compounds and methods described herein.

Example 1: Administration of Quinidine/Oxycodone/Dextromethorphan Treats Restless Leg Syndrome A combination of quinidine/oxycodone (or other μ-opioid agonist)/dextromethorphan is administered to a subject suffering from restless leg syndrome. The subject reports the lessening of pain in the legs and the reduction in the sensation of pins and needles sensation. The subject also reports the lessening of the need to move the legs at night to alleviate the uncomfortable sensations.

Example 2

A patient presented with chronic symptoms that led to a diagnosis of restless leg syndrome ("RLS"). The patient was previously treated with a combination of drugs including a μ-opioid agonist at a dose of 100 mg once a day. Although the treatment was initially successful, the RLS symptoms returned both in frequency and severity likely due to augmentation phenomenon. A combination of dextromethorphan and quinidine was added to the the μ-opioid agonist treatment and the dose of the μ-opioid agonist was cut in half. After 10 days the patient reported significant relief of RLS symptoms, which was confirmed in a follow-up telephone consultation with the patient's physician. Accordingly, the combination of the opioid agonist and the dextromethorphan and quinidine was successful in the treatment of the patient. A second patient was treated using a similar regimen and did not report significant relief. Thus, the addition of dextromethorphan and quinidine to the μ-opioid agonist was found to treat RLS in 50% of the subjects treated while at the same time reducing the amount of the μ-opioid agonist necessary to treat the symptoms of RLS. This result was surprising and unexpected and led to the unexpected ability to reduce the usage (amount) of a μ-opioid agonist.

While the compounds, composition, and methods described herein have been described with reference to examples, those skilled in the art recognize that various modifications may be made without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A method of treating restless leg syndrome or symptoms thereof in a subject comprising administering to the subject a pharmaceutical oral dosage form consisting of dextromethorphan, or a pharmaceutically acceptable salt thereof, quinidine, or a pharmaceutically acceptable salt thereof, and morphine, or a pharmaceutically acceptable salt thereof.

2. The method of claim 1, wherein the subject suffers from augmentation of restless leg syndrome.

3. A method of increasing sleep in a subject with restless leg syndrome, the method comprising administering to the subject a pharmaceutical oral dosage form consisting of dextromethorphan, or a pharmaceutically acceptable salt thereof, quinidine, or a pharmaceutically acceptable salt thereof, and morphine, or a pharmaceutically acceptable salt thereof.

4. The method of claim 1, wherein the ratio of morphine, or a pharmaceutically acceptable salt thereof, to dextromethorphan, or a pharmaceutically acceptable salt thereof, to quinidine, or a pharmaceutically acceptable salt thereof, is about 1:1:1 (wt:wt:wt).

5. The method of claim 3, wherein the ratio of morphine, or a pharmaceutically acceptable salt thereof, to dextromethorphan, or a pharmaceutically acceptable salt thereof, to quinidine, or a pharmaceutically acceptable salt thereof, is about 1:1:1 (wt:wt:wt).

\* \* \* \* \*